United States Patent [19]

Morgan et al.

[11] Patent Number: 4,875,929

[45] Date of Patent: * Oct. 24, 1989

[54] AQUEOUS SUSPENSION CONCENTRATE COMPOSITIONS

[75] Inventors: Leonard J. Morgan; Mark Bell, both of Fareham, England

[73] Assignee: American Cyanamid Company, Stamford, Conn.

[*] Notice: The portion of the term of this patent subsequent to Oct. 3, 2006 has been disclaimed.

[21] Appl. No.: 45,458

[22] Filed: May 7, 1987

Related U.S. Application Data

[63] Continuation-in-part of Ser. No. 867,107, May 23, 1986, abandoned.

[51] Int. Cl.$^4$ .............................................. A01N 33/08
[52] U.S. Cl. .......................................... 71/121; 71/92; 71/93; 71/105; 71/109; 71/118; 71/120; 71/DIG. 1
[58] Field of Search ............................ 71/121, DIG. 1

[56] References Cited

U.S. PATENT DOCUMENTS

| | | | |
|---|---|---|---|
| 3,948,636 | 4/1976 | Marks | 71/DIG. 1 |
| 4,077,795 | 3/1978 | Cooke et al. | 71/121 |
| 4,082,537 | 4/1978 | Dudkowski | 71/121 |
| 4,266,965 | 5/1981 | Simons | 71/DIG. 1 |
| 4,594,096 | 6/1986 | Albrecht et al. | 71/DIG. 1 |
| 4,678,503 | 7/1987 | Barlet et al. | 71/DIG. 1 |

OTHER PUBLICATIONS

The Merck Index, Tenth Edition, Merck & Co., Inc., p. 1016, #6936, 1983.

*Primary Examiner*—Richard L. Raymond
*Assistant Examiner*—Susan P. Treanor
*Attorney, Agent, or Firm*—Estelle J. Tsevdos

[57] ABSTRACT

The present invention relates to novel stable aqueous suspension concentrate or aqueous flowable compositions of the low-melting dinitroaniline pesticide, pendimethalin, alone or in combination with secondary pesticide(s) melting at temperatures greater than 70° C. or pesticides which are water soluble. Additionally are provided methods for preparing the compositions of the invention.

12 Claims, No Drawings

AQUEOUS SUSPENSION CONCENTRATE COMPOSITIONS

This application is a continuation-in-part of application Ser. No. 06/867,107, filed May 23, 1986, abandoned.

BACKGROUND OF THE INVENTION

Suspension concentrate pesticidal compositions or aqueous flowable compositions are concentrated suspensions of water-insoluble pesticides and mixtures of pesticides in an aqueous system. The present invention relates to stable such pendimethalin compositions.

These aqueous compositions frequently contain about 10% to 80%, by weight, of a solid pesticide or mixture of solid pesticides, thereby providing a method for handling those pesticides which are relatively water insoluble in an aqueous medium. Since these types of compositions have the desirable characteristics of a thick liquid, they may be poured or pumped. Thus, some of the problems, like dusting that is possible in solid compositions of wettable powders and granulars, are avoided. Further, these aqueous-based concentrates also have the added advantage of not requiring the use of organic solvents, often present in emulsifiable concentrates.

For these reasons, it is desirable to formulate pesticides into suspension concentrates or aqueous flowables. However, such formulations have their own problems such as gelling, caking and settling, as well as problems because of the physical and chemical characteristics of the pesticide or mixture of pesticides. For instance, the dinitroaniline, pendimethalin, is somewhat difficult to formulate and several references have tried to address these formulation problems.

The problems associated with the development of suspension concentrate compositions containing low melting active ingredients, alone or in combination with higher melting active ingredients, are described in German Patent Application DE 3302648 A1. German Patent Application DE 3302648 A1 tries to deal with the problems of an aqueous mixed dispersion of a low melting active ingredient in a solvent of phthalic acid $C_1$-$C_{12}$ alkyl esters in combination with an aqueous suspension concentrate containing one or more active ingredients as an alternative to a suspension concentrate containing low melting active ingredients, such as pendimethalin[N-(1-ethylpropyl)-2,6-dinitro-3,4-xylidine]. The reason for the alternative approach of that application is the inability to prepare stable suspension concentrates by various techniques, including those of European Patent Application 0 33291 2. That EPO application describes insecticidal suspension concentrate compositions of phosalone and adjuvants which may be prepared with molten insecticide.

Pendimethalin is difficult to formulate not only in a suspension concentrate, but in other forms, as well for several reasons. One is that polymorphic crystals of pendimethalin exist, orange macrocrystals and yellow microcrystals, with the orange form being favored. In formulating pendimethalin in other than suspension concentrates, stabilized pendimethalin had to be used. U.S. Pat. Nos. 4,082,537 and 4,150,969 respectively disclose compositions containing either a sodium dialkyl ($C_6$-$C_8$) sulfosuccinate or an ethoxylated $\beta$-diamine as described. These patents describe the use of sulfosuccinates and $\beta$-diamines in order to stabilize pendimethalin's crystal form to the yellow form and to formulate it in a wettable powder composition.

Not only does pendimethalin exist in two crystal forms, but further crystallization occurs when pendimethalin is finally formulated. These formulations often exhibit stability problems related to rapid crystal formation of final product. Very large, elongated crystals (about 3,000 microns in length) are formed in final formulations which result in instability. Thus, formulating compositions wherein these elongated crystals do not develop is crucial to stability of pendimethalin compositions and is necessary to obtain even distribution of active compound for application.

It is an object of the present invention, therefore, to provide stable aqueous suspension concentrate compositions or aqueous flowable compositions of the low-melting dinitroaniline, pendimethalin, either alone or in combination with other pesticides. Although any secondary pesticide may be used, those having higher melting points or pesticides which are water soluble are suited to the compositions of this invention. Further, it is an additional object of the present invention to provide methods for preparing such stable aqueous suspension concentrate compositions or aqueous flowable compositions so that the final compositions do not result in formation of elongated crystals which interfere with processing and active component efficacy for application.

These and other objects will become more apparent by the detailed description of the invention provided herein.

SUMMARY OF THE INVENTION

The present invention relates to stable aqueous suspension concentrate compositions or aqueous flowable compositions comprising pendimethalin, alone or in combination with other pesticides. Although most secondary pesticides can be used, those having melting points greater than 70° C. or pesticides which are water soluble are suited in the compositions of the invention. Typically, the compositions of the invention comprise, on a weight to volume basis, about 5.0% to 50.0% pendimethalin; about 0% to 50.0% of one or more secondary pesticide(s); about 3.0% to 30.0% coformulants, as described in more detail hereinbelow; and about 20.0% to 92.0% water.

The stable compositions of the invention are readily prepared by forming an emulsion of molten pendimethalin in water containing the coformulants, surfactants, dispersing and/or wetting agents, antifoaming agents and suspending agents. This emulsion has an average droplet size in a range of less than 2 microns to about 10 microns, preferably 2 microns to 6 microns. This is then cooled and optionally milled to obtain an average particle size of suspended particles of less than 20 microns, preferably less than 5 microns.

DETAILED DESCRIPTION OF THE INVENTION

Preferred compositions of the invention comprise on a weight to volume basis, about 5.0% to 50.0% pendimethalin; about 0% to 50.0% of one or more secondary pesticide(s) having a melting point greater than 70° C. or being water soluble; about 3.0% to 30.0% of coformulants, such as surfactants, dispersing agents, wetting agents, antifreezing agents, antifoaming agents, thickening agents, gums, preservatives and 20.0% to 92.0% water.

Coformulants

Pesticides suitable for use in the composition of the present invention include ureas, triazines, imidazolinones, alone or in combination, amongst just a few. Fungicides, insecticides and plant growth regulators which have melting points greater than 70° C. and/or possess physical properties which are amenable to the preparation of aqueous suspension concentrate compositions also may be used in the compositions of the present invention.

Additionally, water-soluble pesticides, such as difenzoquat, amine salts, alkali or alkali metal salts of ioxynil, bromoxynil, phenoxy acetic acids, and imidazolinyl carboxylic acids such as 2-(4-isopropyl-4-methyl-5-oxo-2-imidazolin-2-yl)-3-quinolinecarboxylic acid and the like may readily be incorporated into the stable aqueous suspension concentrate compositions of this invention.

Preferred higher melting (greater than 70° C.) components for use in the aqueous suspension compositions of the invention containing pendimethalin include: Isoproturon, [N,N-dimethyl-N'-(4-(1-methylethyl)phenyl)urea]; Linuron, [N-(3,4-dichlorophenyl)-N'-methoxy-N'methyl urea]; Metoxuron, [N'-(3-chloro-4-methoxyphenyl)N,N-dimethylurea]; Chlortoluron, [N'-(3-chloro-4-methyl-phenyl)-N,N-dimethylurea]; Atrazine, [2-chloro-4-ethyl-amino-6-isopropylamino-1,3-5-triazine]; Imidazolinone herbicides such as 2-(4-isopropyl-4-methyl-5-oxo-2-imidazolin-2-yl)-3-quinolinecarboxylic acid and water soluble salts thereof, and the isomeric mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)toluate. Other secondary active components include terbutylazine, 2-tert-butylamino-4-chloro-6-ethylamino-1,3,5-triazine and metolachlor, 2-chloro-6'-ethyl-N-(2-methoxy-1-methylethyl)acet-o-toluidide.

Surfactants (including dispersing agents and/or wetting agents) suitable in the aqueous suspension compositions of the invention containing solid pendimethalin include: ethylene oxide/propylene oxide condensates; alkyl, aryl- and aryl, arylethoxylates and derivatives thereof; lignosulfonates; cresol- and naphthaleneformaldehyde condensates and sulfonates; polycarboxylates and derivatives thereof; and mixtures thereof.

In general, anionic polymerics, such as cresol formaldehyde condensates and their sulfonates, naphthalene formaldehyde condensates and their sulfonates and lignosulfonates have been found to minimize crystal formation during storage and as such, are most preferred.

Suspending agents such as polysaccharide gums like Xanthan gum, guar gum; gum arabic and cellulose derivatives, and the like are suitable for addition to the hot emulsion in amounts of about 0.02% to 3.0%, on a weight to volume basis. These aid in stabilizing the emulsion of a desired droplet size by increasing the viscosity of the emulsion from an initial viscosity of about 100 cps to about 1,000 cps or greater prior to cooling.

Preservatives to prevent microbial spoiling of the compositions of the invention are included as necessary. One example is a 38% solution of formaldehyde. Other preservatives include methyl and propyl parahydroxybenzoate, 2-bromo-2-nitro-propane-1,3-diol, sodium benzoate, glutaraldehyde, O-phenylphenol, benziso-thiazolinones, 5-chloro-2-methyl-4-isothiazolin-3-one, pentachlorophenol, 2-4-dichlorobenzylalcohol, mixtures thereof and others known to those in the art. Siliconic antifoaming agents are useful in the present compositions.

Antifreezing agents such as ethylene glycol, propylene glycol, other glycols, glycerine or urea may then be added to the resulting aqueous suspension concentrate compositions. Additional surfactants, preservatives and thickening agents, such as clays, precipitated silicas, polyvinyl alcohol, polyvinylpyrrolidone, polyacrylamides and the like, may then be added, as can higher melting active components or a suspension concentrates containing other active components.

Process Of Manufacturing

Stable aqueous suspension concentrate compositions of pendimethalin may be prepared by: emulsifying molten pendimethalin in hot water (50° C. to 80° C.) containing a surfactant and antifoaming agent to achieve the desired droplet size. Then a suspending agent is added. The resulting hot emulsion is cooled and agitated, allowing the molten material to solidify. The resulting composition may then be milled, if desired, or additional higher melting active components and coformulants, such as antifreezing agents, surfactants, thickeners, preservatives and the like or a preformed suspension concentrate containing one or more active component and coformulants is added. The aqueous suspension concentrate compositions containing pendimethalin in combination with higher melting or water soluble components may then be subjected to additional milling, if desired.

The above method of preparation lends itself to a variety of optional processing steps, such as (1) molten emulsion followed by cooling with no further processing; (2) molten emulsion followed by cooling and optionally adding other active components and coformulants and then milling; (3) molten emulsion in the presence of higher melting active components with concurrent milling followed by cooling; (4) molten emulsion concurrently milled and cooled, then mixing to allow crystallization and standing ("aging") with or without secondary active components and a second milling.

Alternatively, the molten pendimethalin may be dispersed at ambient temperature in a water solution of coformulants, containing if desired, other higher melting active components, followed by milling.

Compositions

Surprisingly, stable aqueous suspension concentrate compositions of pendimethalin, alone or in combination with other active pesticidal components may be prepared by the above methods containing, on a weight to volume basis:

5.0% to 50% pendimethalin;
0.05% to 1.0% antifoaming agents;
2.0% to 20.0% antifreezing agent;
2.0% to 20.0% surfactants and mixture of surfactants (wetting and dispersing agents);
0.05% to 3.0% thickening agents;
0.01% to 1.0% preservatives;
0.05% to 2.5% suspending agents; and sufficient water to total 100%. These compositions do not form large, elongated crystals after being processed. Therefore, processing and manufacturing is not halted because of the crystal growths. Further, the compositions are stable without sedimentation of active component in these large (3000 micron) crystals and most importantly, the application of these compositions results in an even dispersibility of active component.

The following examples further illustrate the present invention but are not limitative thereof.

EXAMPLES 1-23

Method A

Preparation of stable aqueous suspension concentrate compositions of pendimethalin, alone or in combination with other higher melting herbicides An aqueous solution containing surfactants and antifoaming agents at temperatures 50° C. to 80° C. is prepared. Then, the molten pendimethalin (60° C. to 80° C.) is added and agitated sufficiently to obtain an emulsion having an average droplet size of about 2 microns to 10 microns. This stabilized emulsion is cooled to ambient temperature, allowing the pendimethalin to solidify, whereupon the desired additional coformulants or active components (antifreezing agents, suspending agents, surfactants, pesticides) are added to the resulting aqueous suspension of solid pendimethalin.

The resulting aqueous composition is milled to achieve the desired average particle size of suspended particles of less than 20 microns, preferably less than 5 microns; and finally, additional thickening agents, preservatives, or surfactants, as desired, are admixed with the aqueous composition. This is then packaged as the aqueous suspension composition.

Utilizing the above procedure yields the stable aqueous suspension concentrate compositions listed in Table I.

TABLE I

| Composition | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Pendimethalin (unstabilized) | 26.0 | 26.0 | 23.6 | 20.0 | 12.5 | 26.0 | 26.0 | 26.0 | 26.0 | 26.0 | 20.0 | 20.0 | 26.0 | 23.6 | 40.0 |
| Isoproturon | 26.0 | 26.0 | 23.6 | — | 37.5 | — | 26.0 | 26.0 | 26.0 | 26.0 | — | — | 26.0 | 23.6 | — |
| Chlortoluron | — | — | — | 30.0 | — | — | — | — | — | — | 30.0 | 30.0 | — | — | — |
| Isomeric mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl-toluate | — | — | — | — | — | 12.5 | — | — | — | — | — | — | — | — | — |
| Na+ cresol-formaldehyde condensate | 5.0 | — | 5.0 | — | — | 5.0 | — | — | — | — | — | — | — | — | — |
| Na+ cresol-formaldehyde sulphonated condensate | — | 3.0 | — | 3.0 | 3.0 | — | 3.0 | 3.0 | 3.0 | 3.0 | 3.0 | 3.0 | 3.0 | 7.0 | 5.0 |
| Na+ lauryl sulphate | 0.5 | 0.5 | 0.5 | 0.5 | 0.5 | — | 0.5 | 0.5 | — | — | — | — | 0.5 | — | — |
| Ca++ Lignosulphonate | — | — | — | — | — | 2.0 | 2.0 | — | — | — | — | — | — | — | — |
| Alkyl phenol ethoxylate | — | — | — | — | — | 6.0 | — | — | — | — | — | — | — | — | — |
| Urea | 8.0 | 8.0 | 8.0 | 8.0 | 8.0 | 8.0 | — | — | 8.0 | — | 8.0 | — | 10.0 | 8.0 | — |
| Precipitated silica | 2.0 | 2.0 | 2.0 | 2.0 | 2.0 | 2.0 | 2.0 | 2.0 | 2.0 | 2.0 | — | 2.0 | 2.0 | 2.0 | — |
| Xanthan gum | 0.1 | 0.1 | 0.1 | 0.1 | 0.1 | 0.1 | 0.1 | 0.1 | 0.1 | 0.1 | 0.2 | 0.12 | 0.12 | 0.1 | 0.2 |
| Formaldehyde 38% sol$^n$ | 0.25 | 0.25 | 0.25 | 0.25 | 0.25 | 0.25 | 0.25 | 0.25 | 0.25 | 0.25 | 0.5 | 0.25 | 0.25 | 0.25 | 0.5 |
| Siliconic antifoam | 0.1 | 0.2 | 0.5 | 0.25 | 0.5 | 0.75 | 0.2 | 0.2 | 0.2 | 0.2 | 0.2 | 0.2 | 0.2 | 0.2 | 0.2 |
| Ethylene glycol | — | — | — | — | — | — | 8.0 | 8.0 | — | 8.0 | — | 8.0 | — | — | 8.0 |
| Ethylene oxide/propylene oxide condensate | — | — | — | — | — | — | — | — | — | 2.0 | 2.0 | 2.0 | — | — | — |
| Water | QS | QS | QS | QS | QS | QS | QS | QS | QS | QS | QS | QS | QS | QS | QS |

| Composition | 16 | 17 | 18 | 19 | 20 | 21 | 22 | 23 |
|---|---|---|---|---|---|---|---|---|
| Pendimethalin | 26.0 | 20.0 | 20.0 | 20.0 | 20.0 | 20.0 | 26.0 | 26.0 |
| Isoproturon | 26.0 | — | — | — | — | — | 26.0 | 26.0 |
| Chlortoluron | — | 30.0 | 30.0 | 30.0 | 30.0 | 30.0 | — | — |
| Urea | 8.0 | — | — | — | — | — | — | 10.0 |
| Siliconic antifoam | 0.2 | 0.4 | 0.5 | 0.5 | 0.5 | 0.5 | 0.4 | 0.5 |
| Xanthan gum | 0.2 | 0.05 | — | — | — | 0.05 | — | 0.1 |
| Formaldehyde 38% solution | 0.5 | 0.125 | — | — | — | 0.125 | — | 0.25 |
| Precipitated silica | — | 2.5 | 2.0 | — | — | 2.0 | 2.7 | 2.0 |
| Na+ naphthalene-formaldehyde condensate | 1.5 | — | — | — | — | — | — | — |
| Na+ oleoyl methyl tauride | 1.5 | 1.0 | — | — | — | — | — | — |
| Ethylene oxide-propylene oxide copolymer | — | 5.5 | 2.0 | 2.0 | 2.0 | 3.6 | 6.0 | — |
| Ethylene glycol | — | 8.0 | 8.0 | 8.0 | 8.0 | 8.0 | 8.0 | — |
| Na+ cresol-formaldehyde sulphonate condensate | — | — | 3.0 | 3.0 | 3.0 | — | — | — |
| Na+ carboxymethyl cellulose | — | — | 0.5 | — | — | — | — | — |
| Polyvinylalcohol | — | — | — | 2.0 | — | — | — | — |

TABLE I-continued

|  |  |  |  |  |  |  |  |  |
|---|---|---|---|---|---|---|---|---|
| Polyvinylpyrollidone | — | — | — | — | 2.0 | — | — | — |
| Na+ Lignosulphonate | — | — | — | — | — | 2.0 | — | — |
| China clay | — | — | — | — | — | — | 1.3 | — |
| Calcium chloride | — | — | — | — | — | — | 1.3 | — |
| Na+ polyacrylate | — | — | — | — | — | — | — | 2.0 |
| Propoxylated alkyl-aryl ethoxylate | — | — | — | — | — | — | — | 3.0 |
| Water | Sufficient water to total 100% | | | | | | | |

EXAMPLES 24-44

Method B

Preparation of stable aqueous suspension concentrate compositions of pendimethalin, alone or in combination with other active components An aqueous solution containing surfactant(s) and antifoaming agents is prepared at a temperature of 50° C. to 80° C. Then, the molten pendimethalin (60° C. to 80° C.) is added to the aqueous solution while agitating sufficiently to obtain an emulsion having an average droplet size of about 2 microns to 10 microns. Sufficient suspending agent is added to this to stabilize the thus-formed emulsion, and this is cooled to ambient temperature, allowing the pendimethalin to solidify, whereupon the additional coformulants, as desired, are admixed to the emulsion. This can then be packaged.

Further, a suspension of a pesticide having a melting point greater than 70° C. is prepared and milled to a suitable average particle size (i.e. less than 20 microns, preferably less than 5 microns) or an aqueous solution containing the desired amount of a water-soluble pesticide is prepared.

Either one of these is then admixed with the suspension concentrate composition of pendimethalin prepared hereinabove. Finally, additional thickening agents, preservatives or surfactants, as desired, are added, and this is then packaged as the mixed aqueous suspension concentrate composition.

Utilizing the above procedure yields the stable aqueous suspension concentrate compositions listed in Table II.

TABLE II

| Composition | Example | | | | |
|---|---|---|---|---|---|
|  | 24 | 25 | 26 | 27 | 28 |
| Pendimethalin (unstabilized) | 23.6 | 23.6 | 23.6 | 23.6 | 23.6 |
| Isoproturon | 23.6 | 23.6 | 23.6 | 23.6 | 23.6 |
| Na+ cresol-formaldehyde sulphonated condensate | — | 3.0 | 4.1 | 3.0 | 4.3 |
| Na+ cresol-formaldehyde condensate | 5.0 | — | — | — | — |
| Alkyphenol ethoxylate | — | — | — | — | 8.0 |
| Na+ oleoyl methyl tauride | — | 0.65 | — | — | — |
| Na+ lauryl sulphate | 0.5 | — | — | 0.5 | — |
| Urea | 8.0 | 8.0 | 8.0 | — | 8.0 |
| Ethylene glycol | — | — | — | 8.0 | — |
| Blend of polyalkylene glycol ether and polyoxyethylene alkylaryl ether | — | — | 0.7 | — | — |
| Siliconic antifoam | 0.25 | 0.5 | 0.5 | 0.5 | 0.5 |
| Silica | 2.0 | 2.0 | — | 2.0 | — |
| Xanthan gum | 0.1 | 0.1 | 0.2 | 0.1 | 0.1 |
| Formaldehyde 38% soln | 0.25 | 0.25 | 0.5 | 0.25 | 0.3 |
| Water | QS | QS | QS | QS | QS |

| Composition | Example | | | | |
|---|---|---|---|---|---|
|  | 29 | 30 | 31 | 32 | 33 |
| Pendimethalin (unstabilized) | 20.0 | 20.0 | 20.0 | 26.0 | 30.0 |
| Chlortoluron | 30.0 | 30.0 | — | — | — |
| Isomeric mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-toluate | — | — | 12.5 | 12.5 | — |
| Ammonium 2-(4-isopropyl-4-methyl-5-oxo-2-imidazolin-2-yl)-3-quinolinecarboxylic acid (solution) | — | — | — | — | 5.0 |
| Na+ cresol-formaldehyde sulphonated condensate | 3.0 | 3.6 | — | — | — |
| Na+ cresol-formaldehyde condensate | — | — | 5.0 | 3.0 | — |
| Triethanolamine salt of polyarylaryethoxylate phophate | — | — | — | 1.3 | — |
| Na+ Lignosulphonate | — | — | — | — | 4.0 |
| CA+ Lignosulphonate | — | — | 2.0 | — | — |
| Alkyphenol ethoxylate | — | — | 8.0 | 6.0 | — |
| Na+ lauryl sulphate | 0.5 | — | — | — | — |
| Urea | 8.0 | 8.0 | 8.0 | — | — |
| Ethylene glycol | — | — | — | 5.0 | 8.0 |
| Siliconic antifoam | 0.5 | 0.1 | 0.5 | 0.4 | 0.5 |
| Silica | 2.0 | 0.1 | 2.0 | 2.0 | 0.75 |
| Xanthan gum | 0.1 | 0.2 | 0.1 | 0.1 | 0.1 |
| Formaldehyde 38% soln | 0.25 | 0.5 | 0.25 | 0.25 | 0.25 |
| Glacial acetic acid (to pH 7.4) | — | — | — | — | √ |
| Blend of polyalkylene glycol ether and polyoxyethylene alkylaryl ether | — | 0.55 | — | — | — |
| Water | QS | QS | QS | QS | QS |

TABLE II-continued

| Composition | Example 34 | 35 | 36 | 37 | 38 | 39 |
|---|---|---|---|---|---|---|
| Pendimethalin (unstabilized) | 33.0 | 40.0 | 40.0 | 40.0 | 40.0 | 33.0 |
| Na+ cresol-formaldehyde sulphonated condensate | — | 4.2 | — | — | — | — |
| Na+ cresol-formaldehyde condensate | — | — | 4.7 | — | — | 4.2 |
| Triethanolamine salt of polyarylarylethoxylate phosphate | 3.4 | — | — | — | — | — |
| Na+ Lignosulphonate | — | — | — | 4.8 | — | — |
| Urea | — | — | — | — | — | 13.3 |
| Ethylene glycol | 8.0 | 8.0 | — | — | 5.0 | — |
| Siliconic antifoam | 0.1 | 0.5 | 0.9 | 0.3 | 1.0 | 0.3 |
| Xanthan gum | 0.1 | 0.1 | 0.1 | 0.1 | 0.2 | 0.16 |
| Formaldehyde 38% soln | 0.25 | 0.25 | 0.25 | 0.25 | 0.5 | 0.4 |
| Polycarboxylate derivative | — | — | — | — | 3.0 | — |
| Water | QS | QS | QS | QS | QS | QS |

| Composition | Example 40 | 41 | 42 | 43 | 44 |
|---|---|---|---|---|---|
| Pendimethalin (unstabilized) | 27.3 | 30.0 | 27.3 | 30.0 | 30.0 |
| Atrazine | 18.2 | 20.0 | 18.2 | 20.0 | 20.0 |
| Na+ cresol-formaldehyde sulphonated condensate | 3.4 | 1.65 | 3.4 | 1.65 | 1.65 |
| Triethanolamine salt of polyarylarylethoxylate phosphate | — | — | — | 1.9 | 1.9 |
| Urea | 5.8 | — | — | — | 5.0 |
| Ethylene glycol | — | 5.6 | 5.2 | 5.0 | — |
| Blend of polyalkylene glycol ether and polyoxyethylene alkylaryl ether | 1.34 | 1.26 | 1.2 | — | — |
| Siliconic antifoam | 0.9 | 0.35 | 0.9 | 0.16 | 0.16 |
| Silica | — | 0.5 | — | 0.4 | 0.4 |
| Xanthan gum | 0.2 | 0.1 | 0.2 | 0.1 | 0.1 |
| Formaldehyde 38% soln | 0.5 | 0.25 | 0.5 | 0.25 | 0.25 |
| Water | QS | QS | QS | QS | QS |

EXAMPLES 45 AND 46

Method C

Preparation of stable aqueous suspension concentrate compositions

An aqueous dispersion of surfactants, antifoaming and antifreezing agents, containing, if desired, a solid active component having a melting point greater than 70° C., is prepared or a water soluble active component is prepared at ambient temperatures. The molten pendimethalin (60° C. to 80° C.), with or without additional surfactants, is then added to the agitated aqueous mixture. This resulting aqueous mixture is milled to achieve the desired average particle size of suspended solids, less than 20 microns, preferably less than 5 microns, and additional thickening agents, suspending agents, preservatives, antifreezing agent and surfactants, as desired, are admixed to the milled composition. This is then packaged as the resulting stable aqueous suspension concentrate composition.

Utilizing the above procedure yield the stable aqueous concentrate compositions listed in Table III.

TABLE III

| Composition | Example 45 | 46 |
|---|---|---|
| Pendimethalin (unstabilized) | 26.0 | 26.0 |
| Isoproturon | 26.0 | 26.0 |
| NA+ cresol-formaldehyde sulphonated condensate | 3.0 | — |
| Polyarylarylpolyoxyethylene phosphate, acid form | — | 5.0 |
| Siliconic antifoam | 0.2 | 0.2 |
| Xanthan gum | 0.2 | 0.12 |
| Formaldehyde 38% solution | 0.5 | 0.5 |
| Ethanediol (Ethylene glycol) | 8.0 | — |
| Water | QS | QS |

EXAMPLES 47 AND 48

Methods A and E

Preparation of stable aqueous suspension concentrates of pendimethalin via the method of the invention versus the method of milling while cooling an emulsion (Method E)

An aqueous suspension concentrate composition of pendimethalin was prepared according to Examples 1-23, Method A. As a comparision, a suspension concentrate of pendimethalin was prepared according to the description of EPO Application 033291.2.

A mixture of hot water (575 cc), ethylene glycol (50 g) and an anionic surface-active agent (a mixture of the monophosphate and the diphosphate of tristyrylphenol with a polyoxyethylene of 18 oxyethylene units, neutralized with triethanolamine, marketed under the tradename of Soprophor FL ® by Rhone-Poulenc) (50 g) is vigorously agitated while 400 g of pendimethalin are added. This is then ground in a dyno mill with a jacket for rapid cooling, resulting in a mixture leaving the mill at 24° C. and having a particle size of 98% less than 5 microns, indicating the formation of a suspension concentrate.

A Xanthan gum biopolymer of a heteropolysaccharide type (1.5 g), produced by fermentation of *Xanthomonas campestris* on carbohydrates (tradename Rhodopol XB 23 marketed by Rhone-Poulenc), is added.

Table IV summarizes the stability observations of the two compositions. The milling method does not avoid the appearance of elongated crystals even upon two short periods of storage, one three day storage at 15° C. and one three day storage at 28° C.

TABLE IV

| Method A - Method of the Invention | | | Method E - Milling while cooling* | | |
|---|---|---|---|---|---|
| Composition | % w/v | Result | Composition | % w/w | Result |
| Pendimethalin | 40 | (1) After six weeks at 28° C. 95% of the particles have an average particle size of less than 15 × 4 microns. | Pendimethalin | 40 | Two tests: (1) Large crystals particle size up to 80 × 5 microns appeared after three days at 15° C. and also when stored at three days at 28° C. |
| Suspending agent Xanthan gum (added prior to cooling) | 0.02 | | Suspending agent Xanthan gum (added after milling and cooling) | 0.15 | |
| Surfactants Sulfonated cresol formaldehyde condensate | 4.0 | | Surfactants mixture of mono and di phosphate of tristyrylphenol neutralized with triethanolamine (Soprophor ® FL) | 5.0 | |
| Polyethoxylated-polymethylmethacrylate | 3.0 | | | | |
| Antifreeze Urea | 5.0 | | Antifreeze Ethylene glycol | 5.0 | |
| Antifoam Siliconic | 0.5 | | | | |
| Preservative Benzisothiazolone | 0.1 | | | | |

® Trademark of Soprosoie, Division of Rhone-Poulenc.
*Particle size found in initial suspension concentrate composition is 98% less than five (5) microns.

EXAMPLES 49-50

Compositions containing active compound of the invention

An aqueous suspension concentrate composition of pendimethalin with a secondary pesticide was prepared according to Examples 1-23 containing the following components:

| | (% w/v) | |
|---|---|---|
| | Formula X | Formula Y |
| Pendimethalin | 23.6 | 20.0 |
| Isoproturon | 23.6 | — |
| Clortoluron | — | — |
| Na cresol-formaldehyde Sulphonated condensate surfactant | 4.1 | 4.14 |
| Polycarboxylate surfactant | — | 1.64 |
| Blend of polyalkylene glycol ether and polyoxyethylene alkyl aryl ether | 0.71 | — |
| Urea | 8.0 | 8.0 |
| Xanthan gum | 0.2 | 0.2 |
| 30% siliconic antifoam | 0.5 | 0.3 |
| Benzisothiazolinone | — | 0.033 |
| Methyl paraben | 0.1 | — |
| Propyl paraben | 0.05 | — |
| Water To | 100% | 100% |

EXAMPLES 51-52

Compositions using hot emulsion double milling process

A hot emulsion of molten pendimethalin is prepared as in Examples 1-23 wherein hot pendimethalin is added to the hot solution of surfactant whilst mixing at high shear. The temperature is 50° C. to 80° C. with a particle size of 2μ to 5μ. The hot emulsion is then milled through a Dyno-Mill and exits as a shattered crystalline form (temperature into mill is about 65° C., and temperature exiting is about 20° C. to 25° C.). This mixture is allowed to "age" to allow orange polymorph crystal conversion. Following conversion, usually 0.5 to 48 hours, a second milling in a Dyno-Mill occurs. (In the event another active pesticide is added, it is added into the aging period stage). Once milled a second time, final coformulants are added.

The following compositions are prepared according to the above procedures.

| | Concentrate % w/w |
|---|---|
| Pendimethalin technical | 40.0 |
| Soprophor ® FL surfactant | 5.0 |
| Silnaolapse ® 500 | 0.5 |
| Propylene glycol | 7.0 |
| Water To | 100% |

This is formulated into the following:

| | 8/1 |
|---|---|
| Concentrate from above | 1000 |
| Rodopol 2% gel | 70 |
| Water To | 100% |

| | % w/v |
|---|---|
| Concentrate from above | 75.0 |
| Atrazine technical | 20.0 |
| Soprophor ® FL | 1.25 |
| Proplyene glycol | 1.25 |
| Water To | 100% |

What is claimed is:

1. An aqueous suspension concentrate composition comprising, on a weight to volume basis: about 5.0% to 50.0% solid pendimethalin; about 3.0% to 30.0% non-pesticidal coformulants; and about 20.0% to 92.0% water.

2. A composition according to claim 1, wherein the coformulants are surfactants; dispersing agents; wetting agents; suspending agents; antifreezing agents; antifoaming agents; thickening agents; and preservatives.

3. A composition according to claim 2, wherein the surfactants, dispersing agents and wetting agents are ethylene oxide/propylene oxide condensates; alkyl,aryl- or aryl,aryl-ethoxylates or derivatives thereof; lignosulfonates; cresol-formaldehyde condensates or sulfonates; naphthalene-formaldehyde condensates or sulfonates; polycarboxylates or their derivatives; and mixtures thereof.

4. A composition according to claim 3, wherein the suspending agents are polysaccharide gums or cellulose derivatives.

5. A composition according to claim 4, wherein the polysaccharide gums are Xanthan gum, guar gum, gum arabic, or mixtures thereof.

6. A composition according to claim 5, wherein the antifreezing agents are ethylene glycol, propylene glycol, glycerine, urea, or mixtures thereof.

7. A composition according to claim 6, wherein the thickening agents are clays, precipitated silicas, polyvinyl alcohol, polyvinylpyrrolidone, polyacrylamides, or mixtures thereof.

8. A composition according to claim 7, comprising, on a weight to volume basis: 5.0% to 50.0% pendimethalin; 2.0% to 20.0% surfactants; 0.05% to 2.5% suspending agents; 2.0% to 15.0% antifreezing agents; 0.05% to 2.0% thickening agent; and 0.05% to 2.5% preservatives.

9. A composition according to claim 8, wherein the antifoaming agent is a siliconic antifoaming agent.

10. A composition according to claim 9, wherein the preservative is a 38% formaldehyde solution, methyl or propyl parahydroxybenzoate, 2-bromo-2-nitro-propane-1,3-diol, sodium benzoate, glutaraldehyde, O-phenylphenol, benzisothiazolinones, 5-chloro-2-methyl-4-isothiazolin-3-one, pentachlorophenol, 2-4-dichlorobenzylalcohol, or mixtures thereof.

11. A composition according to claim 9, comprising, on a weight to volume basis: 30.0% to 40.0% pendimethalin; 3.0% to 5.0% sodium cresol-formaldehyde condensate or sodium cresol-formaldehyde sulphonated condensate; 5.0% to 10.0% ethylene glycol or urea; 0.1% to 1.0% antifoaming agent; 0.1% to 0.3% Xanthan gum; 0.2% to 1.0% preservative; and 48.3% to 68.3% water.

12. A composition according to claim 10, comprising, on a weight to volume basis: 40.0% pendimethalin; 5.0% sodium cresol-formaldehyde sulphonated condensate; 8.0% ethylene glycol; 0.5% siliconic antifoaming agent; 0.2% Xanthan gum; 0.5% of a 38% formaldehyde solution and 51.4% water.

* * * * *